United States Patent
Lambert et al.

(10) Patent No.: US 7,095,501 B2
(45) Date of Patent: Aug. 22, 2006

(54) ETHYL ALCOHOL SENSOR AND METHOD OF USE

(75) Inventors: David K. Lambert, Sterling Heights, MI (US); Mark E Myers, Bloomfield Hills, MI (US); Galen Bruce Fisher, Bloomfield Hills, MI (US); Michel F. Sultan, Troy, MI (US); Taeyoung Han, Bloomfield Hills, MI (US)

(73) Assignee: Delphi Technologies, Inc., Troy, MI (US)

( * ) Notice: Subject to any disclaimer, the term of this patent is extended or adjusted under 35 U.S.C. 154(b) by 192 days.

(21) Appl. No.: 10/348,496

(22) Filed: Jan. 21, 2003

(65) Prior Publication Data

US 2004/0141171 A1 Jul. 22, 2004

(51) Int. Cl.
*G01N 21/00* (2006.01)

(52) U.S. Cl. .................. 356/439; 356/437

(58) Field of Classification Search ........ 356/436, 356/437, 438, 439, 440, 441, 442; 422/84; 600/532; 73/23.3; 436/132; 180/272
See application file for complete search history.

(56) References Cited

U.S. PATENT DOCUMENTS

| | | | | |
|---|---|---|---|---|
| 3,815,087 A | * | 6/1974 | Hirano et al. ............ 180/272 |
| 3,897,679 A | * | 8/1975 | Guild ...................... 73/61.52 |
| 5,261,270 A | | 11/1993 | Gonze et al. |
| 6,171,378 B1 | | 1/2001 | Manginell et al. |
| 6,319,724 B1 | * | 11/2001 | Lewis et al. ................. 436/149 |
| 6,735,506 B1 | * | 5/2004 | Breed et al. .................. 701/36 |
| 6,738,697 B1 | * | 5/2004 | Breed ........................... 701/29 |
| 6,902,701 B1 | | 6/2005 | Hughes et al. |
| 6,946,966 B1 | * | 9/2005 | Koenig ........................ 340/576 |

* cited by examiner

*Primary Examiner*—Hoa Q. Pham
*Assistant Examiner*—Roy M. Punnoose
(74) *Attorney, Agent, or Firm*—Stefan V. Chmielewski

(57) ABSTRACT

An ethanol sensing unit and a method of using, wherein the unit is particularly suitable for use in a confined environment such as the passenger compartment of a passenger vehicle. The sensing unit comprises a device for collecting ethanol vapors while the device is at a first temperature, a device for heating the collecting device to a second temperature higher than the first temperature so as to release ethanol vapors from the collecting device, and a device for sensing the ethanol vapors released from the collecting device when heated by the heating device. The sensing unit is also adapted to delay the operation of the heating device until a period of time sufficient for the collecting device to adsorb ethanol vapors from air contained in the confined environment.

28 Claims, 1 Drawing Sheet

ETHYL ALCOHOL SENSOR AND METHOD OF USE

CROSS REFERENCE TO RELATED APPLICATIONS

Not applicable.

STATEMENT REGARDING FEDERALLY SPONSORED RESEARCH

Not applicable.

BACKGROUND OF THE INVENTION (1) Field of the Invention

The present invention generally relates to sensing devices capable of detecting ethyl alcohol (ethanol). More particularly, this invention relates to an ethanol sensor capable of operating passively to determine the level of intoxication of a person in a confined space, such as the passenger compartment of a motor vehicle.

(2) Description of the Related Art

Intoxicated drivers cause about one third of the fatal automobile accidents that occur in the United States. Because any decrease in the frequency or severity of such accidents would be of considerable benefit, various efforts have been undertaken to develop sensors that detect the blood alcohol content (BAC) or, more typically, the breath alcohol content (BrAC), of drivers as an input to vehicle safety systems. U.S. Pat. No. 4,039,852 is representative of one type of sensor, in which the driver is required to blow into a collection tube before the vehicle can be operated. U.S. Pat. No. 5,907,407 is representative of what may be termed a passive sensing system, in which air from the passenger compartment is automatically drawn to a sensing device, such that the driver's natural exhalation is the basis for sensing the driver's BrAC, from which BAC can be determined. Another example of an alcohol sensor in use is a sensor built into a flashlight or clipboard that a police officer can insert into a vehicle passenger compartment to detect the presence of alcohol vapors in the passenger compartment. The alcohol sensing element used is typically based on an electrochemical detection method. The sensing element typically has two electrodes on a proton-conducting solid polymer electrolyte, such as NAFION, a perfluorinated polymer membrane commercially available from E. I. duPont de Nemours and Company. Such sensing elements are described, for example, in U.S. Pat. No. 4,820,386.

In addition to fuel cells, various other types of sensing elements capable of detecting ethanol vapors are known. For example, the above-noted U.S. Pat. No. 5,907,407 utilizes a laser spectroscopy technique to detect the presence of ethanol vapors, while U.S. Pat. No. 4,039,852 makes use of an alcohol-sensitive element whose electrical resistance decreases when subjected to an alcohol-containing atmosphere. Sensing elements of the latter type include those that measure the conductivity of a tin oxide film, which in addition to responding to ethanol vapors also responds to other species, reducing the accuracy of the sensor.

There is an ongoing need for sensors capable of reliably detecting the alcohol impairment of an individual, and particularly for such a sensor capable of use in a passive on-vehicle sensing system to detect the impairment of a driver.

BRIEF SUMMARY OF THE INVENTION

The present invention is directed to an ethanol sensing unit and a method and system for using the sensing unit, in which the sensing unit, method and system are particularly suitable for use in a confined space, such as the passenger compartment of an automobile.

Generally, the ethanol sensing unit of this invention comprises means for collecting ethanol vapors while the collecting means is at a first temperature, means for heating the collecting means to a second temperature higher than the first temperature so as to release ethanol vapors from the collecting means, and means for sensing the ethanol vapors released from the collecting means when heated by the heating means. The sensing unit also includes means for delaying the operation of the heating means until a period of time sufficient for the collecting means to collect a desired amount of ethanol vapors from air contained in a surrounding environment. As such, the sensing unit makes possible a method of sensing ethanol vapors that entails collecting ethanol vapors with the collecting means at a first temperature and, after a period of time sufficient for the collecting means to collect ethanol vapors in an amount sufficient to be quantified, heating the collecting means to a second temperature higher than the first temperature so as to release ethanol vapors from the collecting means. The ethanol vapors released from the heated collecting means are sensed, such that a decision can be made as to whether the level of ethanol vapors present in the surrounding environment is indicative of alcohol impairment of an occupant in the environment.

The above-described method of using the sensing unit of this invention can occur prior to vehicle startup, and/or can be performed repetitively during a trip. Repetitive sensing enables the unit to monitor, for example, for the possibility that previously consumed alcohol will clause the concentration of ethanol in the driver's blood to gradually increase above acceptable limits after vehicle startup, as well as monitor the consumption of alcohol in the vehicle while it is being driven. In either case, the sensing unit of this invention is able to operate passively, in that it does not require any active participation by the person(s) being assessed (e.g., driver and other passengers of a vehicle) beyond normal breathing. Instead, using a passenger vehicle as an example, the sensing unit collects a representative sample of ethanol from the driver's breath through sampling of air from the passenger compartment, which is then analyzed to quantify the concentration of alcohol in the sample. This quantity can be used to determine whether the driver is impaired. The output of the sensing unit is enhanced by collecting ethanol from the air over a period of time and then releasing collected ethanol vapors over a shorter period of time or in some other manner that results in the released vapors being at a higher concentration than in the sampled air. The analysis of a more concentrated sample improves the reliability of the sensing unit over prior art sensors that simply use a sensor element to measure the concentration of ethanol vapors in a vehicle passenger compartment.

In the case where the surrounding environment of interest is the passenger compartment of an automobile, additional inputs to the decision criteria can include the state of the heat-ventilation and air-conditioning (HVAC) system of the vehicle during sample collection, ambient temperature, number of passengers, the operation of other vehicle systems that might affect the concentration of ethanol vapors in the passenger compartment or introduce compounds that lead to a false positive reading, etc.

Alternatively or in addition, the output of the sensing unit can be used as an input to an on-board vehicle safety system that is programmed to alter the operation of the vehicle in a manner that reduces the risk and/or severity of an accident. In general, the safety consequences of drunk driving are caused by extra risk taking and by impaired driving performance. To ameliorate the consequences of an impaired driver's slower reaction time, for example, it may be possible to provide more time for the driver to react. For example, if the vehicle is equipped with an active cruise control system that is programmed to provide at least a minimum headway distance behind a preceding vehicle, the preset minimum headway distance could be automatically increased if driver impairment is detected. Furthermore, the safety system could alter the man-machine interface of the vehicle to have a simplified pattern of behavior if driver impairment is detected to reduce driver distraction or confusion. For example, to help avoid the consequences of extra risk taking, the vehicle could be programmed to adjust performance limits or vehicle response times based on the driver's state as a result of detecting driver impairment. As described in SAE Paper 2002-21-0031, future safety systems in vehicles are envisioned to employ data fusion of many inputs to arrive at appropriate response(s) to given situations. Because of the increased likelihood of a fatal accident if a driver is alcohol impaired, the detection of alcohol vapor in the passenger compartment is an important input that can be included as a result of the sensing unit, method and system of this invention. An on-board vehicle safety system equipped with the sensing unit of this invention could be operated on a high level of abstraction so that the detection of alcohol vapor is not used alone to induce a vehicle response, but in combination with one or more other inputs that suggest the same conclusion of driver impairment.

Other objects and advantages of this invention will be better appreciated from the following detailed description.

DETAILED DESCRIPTION OF THE INVENTION

Figure 1:
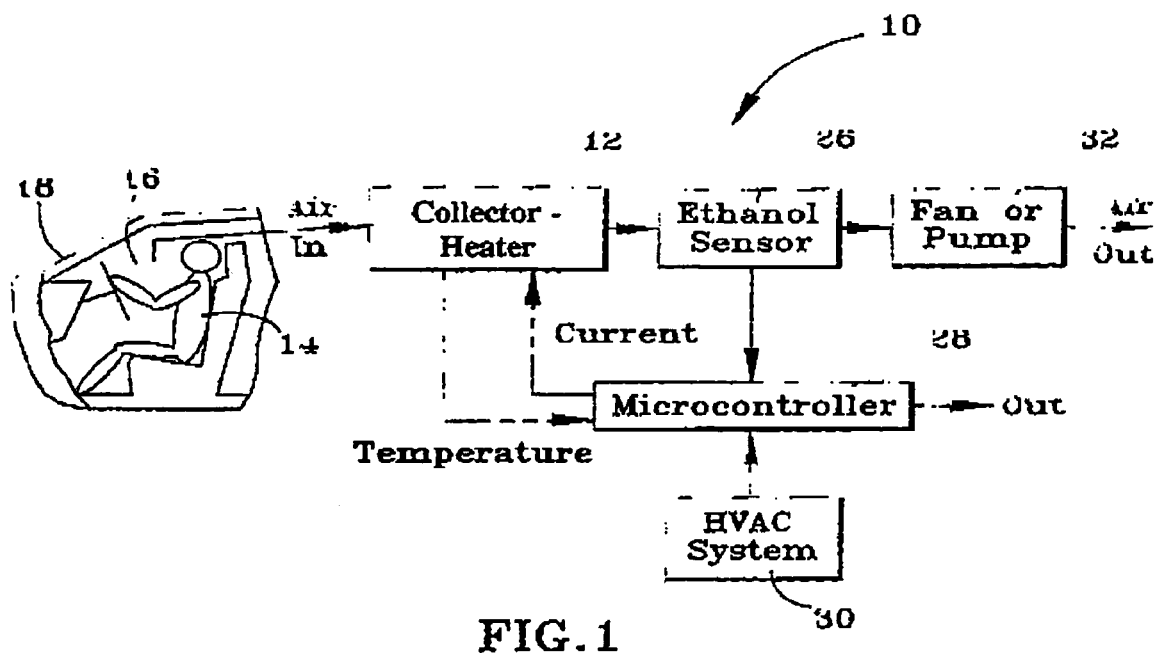
FIG. 1 is a schematic of an ethanol sensing system for a passenger vehicle in accordance with the present invention.

FIG. 1 represents an ethanol sensing system 10 that makes use of a collector/heater unit 12 in accordance with a preferred embodiment of this invention. As schematically represented, the system 10 operates to collect a representative sample of ethanol from the breath of a driver 14 (and potentially other occupants) within the passenger compartment 16 of a passenger vehicle 18, and then to quantify the amount of ethanol collected to determine whether the driver 14 is impaired. While the following description will focus on the use of the system 10 with a passenger vehicle 18, the teachings of this invention are generally applicable to uses within essentially any confined space where the exhalation of the occupants of the confined space can be sampled to determine the level, if any, of ethanol in the occupants' bodies.

To collect a representative sample, air from the passenger compartment 16 (mixed with the exhaled breath from the driver 14) is passed over the collector/heater unit 12. As depicted in FIG. 1 a fan or pump 32 can be employed to draw air over the collector/heater unit 12, though it is foreseeable that other devices and techniques could be employed. An ethanol sensor 26 is then used to measure the concentration of ethanol in the drawn air sample. The measured concentration is then relayed as a sensor output to a microcontroller 28, where the information is evaluated to determine whether the driver 14 might be impaired by alcohol consumption. The individual components of the system 10 and methods by which they can be operated together to identify driver impairment is discussed in further detail below.

The placement of the unit 12 within the compartment 16 can vary, depending upon stylistic and packaging considerations together with the need to determine driver impairment. In general, there is a dilution factor that relates the concentration of ethanol vapor in the driver's breath to the concentration in the air at the sampling location. A simple comparison between the volumetric flow of fresh air into the vehicle 18 and the rate at which a person at rest exhales breath over a period of time suggests that the average dilution factor will typically be on the order of $10^{-3}$. One potential sampling location is on the ceiling of the vehicle 18 behind the driver's head, since exhaled breath tends to stream past this location. Another potential sampling location is on the surface of the driver's seat. A location near the driver 14 has the advantage that the dilution factor can be enhanced over the average dilution factor in the vehicle 18. A location near the driver 14 may also preferentially sample breath from the driver 14 as opposed to passengers to avoid a false detection of driver impairment if the ethanol vapor is actually from another passenger in the vehicle 18. Another aspect of sampling air near the driver 14 is that both ethanol and $CO_2$ concentrations can be measured, allowing for a more quantitative measure of the driver's breath alcohol concentration (BrAC). Specifically, exhaled breath contains about 3.5% $CO_2$ while ambient air only contains about 400 ppm $CO_2$. With this knowledge, the measured $CO_2$ concentration in a sample would indicate the concentration of breath in the sample. Another option is to configure the unit 12 to sample air from two locations, one of which is close to the driver 14 while the other is remote from the driver 14 to serve as a reference. The ethanol concentrations in the two samples could be alternatively determined with the same sensor 26, which would have the benefit of avoiding the effects of sensor drift and verify that driver 14 is the source of the sensed ethanol.

The concentration of ethanol vapors at any given location within the compartment 16 will vary significantly with the distribution of airflow resulting from the existing HVAC mode and the aiming directions of the air-conditioning (AC) outlets located in the compartment 16. Furthermore, drastically different airflow fields and ethanol concentrations would be expected in the compartment 16 depending on whether the HVAC system is operating in the heating, AC or defrost mode. Therefore, another approach is to sample the air away from the driver 14, where it is well mixed with the air of the passenger compartment 16. For example, the air could be sampled at the exit vent (not shown) of the compartment 16. The air escaping through the exit vent would be well mixed with any ethanol vapors exhaled by the vehicle's occupants, and would significantly reduce the variations in ethanol levels under various HVAC operating conditions. Typically a vehicle is equipped with several exit vents at various locations in the compartment 16. By carefully targeting the placement of the sensing unit 12 close to the driver 14, this approach could be tailored to sense ethanol vapors exhaled mainly by the driver 14. Furthermore, sensing at an exit vent would permit the air flow into the compartment 16 (e.g., from an HVAC system 30 represented in FIG. 1 to be used to relate the measured concentration of ethanol to the concentration in the driver's breath. Because this approach would also sense ethanol vapors exhaled by any passengers within the compartment 16, the number of passengers would also preferably be sensed.

Figure 2:
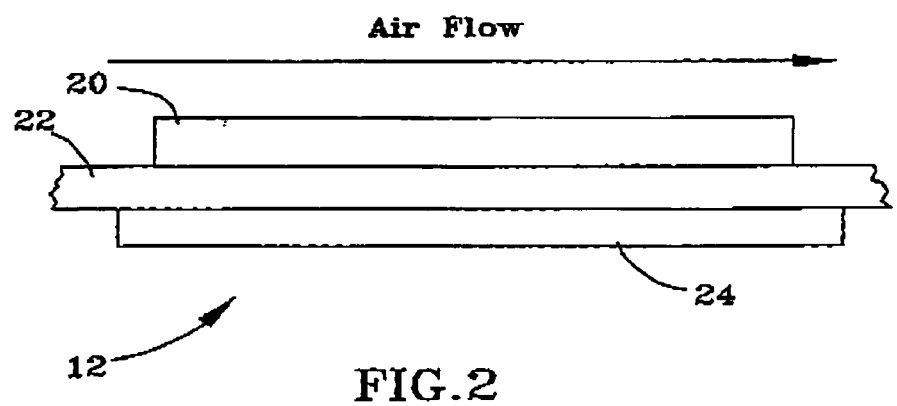
FIG. 2 schematically represents a cross sectional view of an collector/heater unit shown in FIG. 1.

As represented in FIG. 2 the collector/heater unit 12 comprises a collection film 20 on a substrate 22 contacted by a heating element 24. Suitable heating elements 24 include resistive elements, such as those formed by depositing a platinum pattern on a ceramic substrate or as one layer of a multi-layer ceramic device, though other heating devices also known in the art could foreseeably be used. The collection film 20 is chosen on the basis of being capable of collecting, e.g., adsorbing or absorbing, ethanol vapors, and is preferably selective to ethanol vapors over other potential constituents of the sampled air, such as water vapor. Preferred materials for the collection film 20 are adsorbent materials such as carbon molecular sieves, activated carbon materials with a porous graphitic microstructure, porous polymers, and inorganic materials with high surface area, such as a zeolite. It is possible to increase the selectivity of the collector/heater 12 by using more than one film 20, each with a controlled temperature. Materials capable of collecting ethanol will also typically collect methanol, which can be present in the passenger compartment 16 if the windshield washing unit was recently used. Because sensors 26 (discussed in greater detail below) capable of detecting ethanol will also typically sense methanol without distinguishing between the two, the presence of methanol in the passenger compartment 16 can result in a false positive output. To address this situation, the system 10 can use as an input the length of time since the windshield washing unit of the vehicle 18 was used.

During the operation of the sensing system 10, the collection film 20 is maintained at a predetermined temperature for a period of time during which ethanol vapors are collected (i.e., adsorbed or absorbed) by the film 20. Adsorption involves strongly bonding a monolayer of ethanol molecules to the collection film 20 as a result of the film 20 being porous and having a large surface area per unit volume (or mass). As a result of the manner in which ethanol molecules are adsorbed, an adsorbent collection film 20 is able to release adsorbed ethanol molecules at an elevated temperature. An optimal temperature for adsorption of ethanol is believed to be significantly above ambient temperature to ensure that the humidity is not too high. At relative humidity levels above about 65%, adsorbed water vapor is said to change carbon molecular sieve materials from a hydrophobic state to a hydrophilic state, which would circumvent the preferential adsorption of ethanol instead of water vapor.

Following adsorption, the heating element 24 is operated to raise the collection film 20 to a temperature sufficient to release the collected ethanol as a vapor. In accordance with a preferred aspect of the invention, the collection film 20 and the heating element 24 are operative to enable the heating element 24 to rapidly heat the collection film 20 to a temperature sufficient to quickly release as vapors any ethanol adsorbed by the collection film 20. For example, the heating element 24 may be operated to heat the collection film 20 from an adsorption temperature of about 25° C. to a release temperature of about 150° C. within ten seconds or less. The ethanol sensor 26 is then used to measure the concentration of ethanol in the sample, producing an output that is relayed to the microcontroller 28. During analysis of the sample, it is believed to be preferable to stop the flow of air over the collection film 20 before heating to maximize the ethanol concentration in proximity to the sensor 26.

Preferred ethanol sensors 26 are believed to include those presently qualified for on-board vehicular use, such as sensors that detect ethanol vapor by measuring its effect on the electrical conductance of a heated metal oxide film on a ceramic substrate. An example is sensors that employ tin oxide ($SnO_2$) sensing elements, whose chemical selectivity is known to be affected by the chemical composition of the metal oxide film, the microstructure of the film, and temperature. The selectivity of a tin oxide film to ethanol can be improved, for example, by the addition of lanthana ($La_2O_3$) to the tin oxide film. In operation, such sensors typically maintain the metal oxide film at a temperature about 300° C. with an electrical heater embedded in the thin insulating ceramic substrate supporting the film. The sensing element is contained in a package that allows air to enter. For thermal isolation, the sensing element is suspended inside the package by its electrical leads. Metal oxide sensing elements particularly suitable for use as the ethanol sensor 26 of this invention are typically capable of detecting ethanol vapor at levels of as little as about 10 ppm, hence the necessity for the collector/heater unit 12 of this invention to increase the ethanol vapor concentrate from a passively-collected air sample. Commercial sources for such sensors include FiS Inc., 3-36-3 Kitatono, Itami, Hyogo, 664-0891 Japan, Figaro USA Inc., 373 West Lake Ave. Suite 203, Glenview, Ill. USA 60025, and Thermometrics, Inc., 808 US Highway 1, Edison, N.J. USA 08817- 4695.

Silicon-based sensors have also been investigated for measuring ethanol vapor concentrations. Silicon-based sensors fabricated using a standard CMOS integrated circuit manufacturing process have been demonstrated to respond to ethanol. Sensors of this type are described in the following publications: A. Hierlemann et al., "Application-specific Sensor Systems Based on CMOS Chemical Microsensors," Sensors and Actuators B 70 (2000) 2-11; C. Hagleitner et al., "Smart Single-Chip Gas Sensor Microsystem," Nature 414 (2001) 293-296; and J. W. Gardner et al., "Response of a Poly(pyrrole) Resistive Micro-bridge to Ethanol Vapor," Sensors and Actuators B 48 (1998), 289-295. A difficulty with the use of silicon-based sensors is that they also readily absorb water vapor.

Another alternative is an electrochemical sensor, such as those that make use of the NAFION solid polymer electrolyte. While exhibiting greater sensitivity, reportedly about 1 ppb ethanol in air, electrochemical sensors typically have a limited operating life. Other types of ethanol vapor sensors with high sensitivity have also been reported. One approach that reportedly can detect 1 ppm ethanol involves monitoring the light that is given off as ethanol vapor reacts with oxygen at the surface of a catalyst, as reported by M. Nakagawa, "A New Chemiluminescence-based Sensor for Discriminating and Determining Constituents in Mixed Gases," Sensors and Actuators B 29 (1995) 94-100. However, a commercial embodiment of this sensor does not yet appear to be commercially available. Still another potential approach is the use of a field effect transistor (FET) having a thin film of $LaFeO_3$ covering the gate. Such a sensor is said to able to detect about 100 ppm of ethanol, and is reported in S. Zhao et al., "A High Performance Ethanol Sensor Based on Field-effect Transistor Using a $LaFeO_3$ Nano-Crystalline Thin-film as a Gate Electrode," Sensors and Actuators B 64 (2000) 83-87. Other possible ethanol sensors may be based on the infrared transmission of a sample. Still other possibilities include a sensor 26 that measures a change in luminescence caused by the reaction of ethanol vapor, or a sensor 26 that responds to a potential change caused by ethanol adsorption.

Finally, and as discussed above, it may be desirable to measure the concentrations of both ethanol and $CO_2$ in the air sample to quantify the concentration of breath in the sample, allowing for a more quantitative measure of the driver's breath alcohol concentration (BrAC). In practice, an infrared measurement is believed to be preferable for measuring $CO_2$ concentrations, and for this purpose the sensor 26 could incorporate an infrared sensor to assist in the determination of ethanol concentration.

FIG. 1 represents the microcontroller 28 as controlling the collector/heater unit 12 by sensing the temperature of the collection film 20. According to the invention, after an appropriate delay period of typically a few minutes, though possibly as short as about ten or as long as three hundred seconds or more, the microcontroller 28 delivers current or another suitable input to the heating element 24 to quickly heat the collection film 20 to an appropriate elevated temperature. Generally, the delay period should be limited such that the collection film 20 does not become saturated with ethanol or water vapor. The amount of air required to saturate the collection film 20 is defined as the breakthrough volume. To achieve better control with the delay period, it may be preferable to first flow air over the collection film 20 and then rapidly heat the film 20 to release any collected vapors that may have accumulated while the vehicle 18 was unoccupied. The collection film 20 can then be allowed to cool down, such as by continuing the air flow, to a specified temperature, preferably above ambient temperature, at which time the collection film 20 would collect ethanol vapor for the predetermined time interval. At the completion of this time internal, air flow is preferably discontinued and the collection film 20 is rapidly heated with the heating element 24 to release (e.g., desorb) the collected ethanol vapor, which are then sensed with the ethanol sensor 26.

As also represented in FIG. 1, additional inputs to the microcontroller 28 for consideration can include the state of the HVAC system 30 during sample collection and the temperature of the collection film 20. Chemical selectivity of the unit 10 to ethanol can be potentially improved by monitoring the output from the sensor 26 as a function of the temperature of the collection film 20 during the desorption process. Such a technique is known as temperature programmed desorption (TPD), and is discussed in L. Morris et al., "Simple System for Part-per-billion-level Volatile Organic Compound Analysis in Groundwater and Urban Air," Meas. Sci. Technol. 13 (2002) 603–612. For TPD to be able to distinguish between different species, the rate of heating cannot be excessive. TPD is also limited by detector response time and by the need to limit the spacial variation of the adsorber temperature.

Other possible inputs include the ambient temperature of the passenger compartment 16, the operation of other vehicle systems that might affect the concentration of ethanol vapors in the passenger compartment 16 or introduce compounds that lead to a false positive reading, etc. The system 10 can also operate in cooperation with an on-board vehicle safety system (not shown) so that the detection of ethanol vapors is not used alone to induce a vehicle response, but is used in combination with one or more other inputs that are also capable of indicating that the driver 14 is impaired. Such additional inputs can also be utilized by the microcontroller 28 and system 10 as a whole to determine an appropriate response to an elevated ethanol level. For example, the ignition system could be disabled if the vehicle 18 is not moving. If used in combination with an on-board vehicle safety system, the output of the system 10 could be used to alter the operation of the vehicle 18 in a manner that reduces the risk and/or severity of an accident. For example, a vehicle equipped with an active cruise control system could be reprogrammed to increase the minimum headway distance behind a preceding vehicle, the vehicle 18 could be reprogrammed to adjust performance limits or vehicle response times.

In view of the above, the invention makes use of an collection film 20 that takes up ethanol vapor at a first temperature, and then releases the ethanol vapor when heated to a higher temperature. By using an adsorbent film 20 (e.g., carbon molecular sieve, activated carbon material with a porous graphitic microstructure, porous polymer, and/or an inorganic material with high surface area such as zeolite) that is selective to ethanol, coupled with the use of a sensor 26 having a sensing element (e.g., a tin oxide or metal oxide sensor) capable of selectively measuring the concentration of ethanol vapors, the system 10 operates with two sources of selectivity, resulting in the system 10 having better selectivity than would be possible with either alone. Furthermore, the output of the sensor 26, and therefore the output of the microcontroller 28, is enhanced by operating the collector/heater unit 12 to collect ethanol vapors over a relatively extended period of time, such as ten seconds or more, followed by discontinuing air flow and heating the collection film 20 to release the adsorbed ethanol. Alternatively, if airflow were to be continued during desorption, desorption (heating) should be performed more rapidly relative to the adsorption step in order to significantly increase the concentration of released ethanol vapors in the sample analyzed by the ethanol sensor 26. The process of using an extended adsorption period is equivalent to integrating the signal over a period of time, which leads to decreased uncertainty in the measured value. The rapid desorption of that integrated amount in a short time is thereby made easier to measure. As a result, the reliability of the determination of alcohol impairment is improved over the prior art practice of simply using a sensor element to measure the concentration of ethanol vapor in a passenger compartment.

In an investigation relating to the present invention, a multi-bed thermal desorption tube was employed to trap ethanol vapors. The desorption tube used is commercially available under the name CARBOTRAP 300 from Supelco, Bellefonte, Pa. USA, and in the form of a glass tube that contains several different types of carbon adsorbent materials in beds separated by glass wool. The use of multiple adsorbent materials allowed for the collection of a wide range of molecules (classified by carbon number). Ethanol is a C2 material and was expected to be trapped mainly by one of the beds containing a carbon molecular sieve commercially available from Supelco under the name CARBOSIEVE S-III. This material is reported to have a pure carbon framework having a surface area of about 800 $m^2$/g and contain pores with diameters of about 15 to 40 Angstroms. The tube was heated by a Model 785 Tube Conditioner commercially available from Envirochem. This heating device comprised a collar with an inner copper tube that slipped over the desorption tube. Surrounding the copper tube was a woven fibrous material containing a resistive heating element that was capable of heating the copper tube to a temperature of about 150° C. to about 200° C. within a about thirty seconds.

The investigation was intended to demonstrate that the concentration of ethanol vapor could be increased to a more easily detectable level by collecting ethanol on an adsorber and then heating the adsorber. To simulate air mixed with breath from an intoxicated person, pure nitrogen gas was bubbled through an alcohol-water solution. The solution was prepared by adding about 0.1 gram of pure ethanol to about 1 liter of deionized water, giving a concentration of about 0.01 percent, which is about one-tenth the blood alcohol concentration at the threshold of intoxication. The solution was at ambient temperature (about 25° C.) and contained in a flask that was closed with a rubber stopper so that gas entered through a glass tube and bubbled through the solution. A second glass tube through the stopper terminated in the headspace above the solution and removed the discharge vapors. The flow rate was about 25 cc per minute as measured by a rotometer. The discharge flow was allowed to pass through the desorption tube for about two minutes, giving a total flow through the tube of about 50 cc. The concentration of ethanol vapor in the mixture that entered the desorption tube was estimated to be about 19 ppm, calculated from the value of Henry's constant for the alcohol/water solution at 25° C., 0.88 kPa.kg/mol, as reported in J. Ueberfeld et al., "Determination of Henry's Constant Using a Photoacoustic Sensor," J. Chem. Thermodynamics 33 (2001) 755-764.

The tube was removed from the adsorption apparatus and connected to a flame ionization detector (FID) known in the art. The heating element described above was placed around the adsorption tube and heated, reaching about 200° C. in about thirty seconds. A switching-valve confined the desorbed vapors to the connection tubing during this time. The switching-valve was then switched, which allowed nitrogen carrier gas to pass through the tube, connection tubing, and FID. After about six seconds, the FID detector registered a strong peak of about 350 picoamperes. The elution of a blank tube (no ethanol adsorbed) gave a different-shaped peak of about 25 picoamperes. The FID, by nature of its operation, was not sensitive to either water or carbon dioxide. The total interior volume of the collection tube and of the tubing that connected it to the FID was approximately 1.7 cc, while the volume of sample that was passed through the collection tube was about 50 cc as noted above. Thus, at a minimum, ethanol vapor concentration was enhanced by a factor of 29 in this experiment. The active adsorber occupied a volume of only about 0.4 cc within the desorption tube. Thus if only active adsorber were used in the tube, the concentration of ethanol vapor could be increased by more than a factor of 100.

While the invention has been described in terms of a preferred embodiment, it is apparent that other forms could be adopted by one skilled in the art. For example, various materials and devices could be used in place of the disclosed collection film 20, and various means could be used in place of the disclosed ethanol sensor 26 to sense the presence of ethanol vapors released by the collection film 20. Accordingly, the scope of the invention is to be limited only by the following claims.

The invention claimed is:

1. An ethanol sensing unit located in a passenger compartment of a vehicle, the ethanol sensing unit comprising:
   means for collecting ethanol vapors within an air sample taken from the passenger compartment while the collecting means is at a first temperature;
   means for heating the collecting means to a second temperature higher than the first temperature so as to release ethanol vapors from the collecting means;
   means for delaying operation of the heating means for a predetermined period of time during which the collecting means collects ethanol vapors from the air sample; and means for sensing the ethanol vapors released from the collecting
   means when heated by the heating means and providing therefrom an output ethanol concentration signal;
   means for sensing a state of a system of the vehicle that is capable of altering the concentration of vapors in the passenger compartment; and
   means for modifying the output ethanol concentration signal responsive to the sensed state of the system of a vehicle that is capable of altering the concentration of vapors in the passenger compartment to provide a datum indicative of alcohol impairment of a vehicle driver in the passenger compartment.

2. The ethanol sensing unit according to claim 1, wherein the sensing means measures the concentration of ethanol vapors released from the collecting means.

3. The ethanol sensing unit according to claim 1, further comprising means for measuring a concentration of carbon dioxide in the passenger compartment, quantifying a concentration of breath in the passenger compartment based on the concentration of carbon dioxide and modifying the output ethanol concentration signal responsive to the quantified concentration of breath in the passenger compartment.

4. The ethanol sensing unit according to claim 1, wherein the delaying means and the heating means are operative to permit collection of ethanol vapors by the collecting means over a longer period of time than the heating means heats the collecting means to release the ethanol vapors, so that the ethanol vapors released from the collecting means are at a higher concentration than the ethanol vapors within the air sample.

5. The ethanol sensing unit according to claim 1, wherein the collecting means selectively adsorbs ethanol.

6. The ethanol sensing unit according to claim 1, wherein the sensing means selectively senses ethanol.

7. The ethanol sensing unit according to claim 1, further comprising means for flowing the air sample from the passenger compartment over the collecting means.

8. The ethanol sensing unit according to claim 1, wherein the system of the vehicle that is capable of altering the concentration of vapors in the passenger compartment.

9. The ethanol sensing unit according to claim 1, wherein the system of the vehicle that is capable of altering the concentration of vapors in the passenger compartment is a methanol dispensing system.

10. The ethanol sensing unit according to claim 1, wherein the collecting means is configured to be alternatingly subjected to multiple air samples taken from different locations within the passenger compartment, and the sensing means is operable to compare the levels of the ethanol vapors collected from the multiple air samples.

11. A passive ethanol sensing unit located in a passenger compartment of a vehicle, the sensing unit comprising:
   an adsorbent material capable of adsorbing ethanol vapors;
   means for flowing air from the passenger compartment over the adsorbent material to cause adsorption by the adsorbent material of any ethanol vapors contained in the air while the adsorbent material is at a first temperature;
   means for heating the adsorbent material to a second temperature higher than the first temperature so as to release ethanol vapors from the adsorbent material;
   means for delaying operation of the heating means for a predetermined period of time during which the adsorbent material adsorbs ethanol vapors from the air flowed over the adsorbent material by the flowing means;

means for measuring the concentration of the ethanol vapors released from the adsorbent material when heated by the heating means and providing an output ethanol concentration signal based on the measured concentration;

means for sensing a state of a system of the vehicle that is capable of altering the concentration of vapors in the passenger compartment; and means for modifying the output ethanol concentration signal responsive to the sensed state of a system of the vehicle that is capable of altering the concentration of vapors in the passenger compartment to provide a datum indicative of alcohol impairment of a vehicle driver in the passenger compartment.

12. The ethanol sensing unit according to claim 11, further comprising means for measuring a concentration of carbon dioxide in the passenger compartment and quantifying a concentration of breath in the air sample based on the concentration of carbon dioxide and modifying the output ethanol concentration signal responsive to the quantified concentration of breath in the passenger compartment.

13. The ethanol sensing unit according to claim 11, wherein the adsorbent material selectively adsorbs ethanol.

14. The ethanol sensing unit according to claim 11, wherein the system of the vehicle that is capable of altering the concentration of vapors in the passenger compartment.

15. The ethanol sensing unit according to claim 11, wherein the system of the vehicle that is capable of altering the concentration of vapors in the passenger compartment is a methanol-dispensing system.

16. A method of sensing ethanol vapors in a passenger compartment of a vehicle, the method comprising the steps of:

collecting ethanol vapors from an air sample from an air sample taken from the passenger compartment with a collecting means at a first temperature;

after a predetermined period of lime during which the collecting means to collects ethanol vapors from the air sample, heating the collecting means to a second temperature higher than the first temperature so as to release ethanol vapors from the collecting means; sensing ethanol vapors released from the collecting means when heated and providing therefrom an output ethanol concentration signal;

sensing a state of a system of the vehicle that is capable of altering the concentration of vapors in the passenger compartment; and then modifying the output ethanol concentration signal responsive to the sensed state of a system of the vehicle that is capable of altering the concentration of vapors in the passenger compartment to provide a datum indicative of alcohol impairment of a vehicle driver in the passenger compartment.

17. The method according to claim 16, wherein the concentration of ethanol vapors released from the collecting means is measured during the sensing step.

18. The method according to claim 16, wherein the collecting means comprises an adsorbent material chosen from the group consisting of carbon molecular sieves, activated carbon materials with a porous graphitic microstructure, porous polymers, and inorganic materials with high surface area.

19. The method according to claim 16, wherein the sensing step is performed with a sensing means comprising a metal oxide film on a ceramic substrate.

20. The method according to claim 16, wherein collection of ethanol vapors by the collecting means occurs over a longer period of time than the heating of the collecting means to release the ethanol vapors, and the ethanol vapors released from the collecting means are at a higher concentration than the ethanol vapors within the air sample.

21. The method according to claim 16, wherein the collecting means selectively adsorbs ethanol.

22. The method according to claim 16, wherein ethanol is selectively sensed during the sensing step.

23. The method according to claim 16, further comprising the step of flowing the air sample from the passenger compartment surrounding environment over the collecting means.

24. The method according to claim 23, further comprising the step of discontinuing the flowing of the air sample from the passenger compartment over the collecting means during the heating and sensing steps.

25. The method according to claim 16, wherein the system of the vehicle that is capable of altering the concentration of vapors in the passenger compartment is a heat-ventilation and air-conditioning system.

26. The method according to claim 25, wherein the system of the vehicle that is capable of altering the concentration of vapors in the passenger compartment is a methanol-dispensing system.

27. The method according to claim 16, wherein the collecting step comprises alternatingly subjecting the collecting means to multiple air samples taken from different locations within the passenger compartment, and the sensing step comprises comparing the levels of the ethanol vapors collected from the multiple air samples.

28. The A method according to claim 16, further comprising the steps of:

measuring a concentration of carbon dioxide in the passenger compartment;

quantifying a concentration of breath in the air sample based on the concentration of carbon dioxide; and modifying the output ethanol concentration signal responsive to the quantified concentration of breath in the passenger compartment.

* * * * *